(12) United States Patent
Benowitz

(10) Patent No.: US 7,338,666 B2
(45) Date of Patent: *Mar. 4, 2008

(54) METHODS FOR MODULATING THE AXONAL OUTGROWTH OF CENTRAL NERVOUS SYSTEM NEURONS

(75) Inventor: Larry I. Benowitz, Newton, MA (US)

(73) Assignee: Children's Medical Center Corporation

( * ) Notice: Subject to any disclaimer, the term of this patent is extended or adjusted under 35 U.S.C. 154(b) by 0 days.

This patent is subject to a terminal disclaimer.

(21) Appl. No.: 11/132,701

(22) Filed: May 19, 2005

(65) Prior Publication Data

US 2005/0277614 A1 Dec. 15, 2005

Related U.S. Application Data

(63) Continuation of application No. 10/385,031, filed on Mar. 10, 2003, now abandoned, which is a continuation of application No. 09/997,687, filed on Nov. 29, 2001, now abandoned, which is a continuation of application No. 08/921,902, filed on Sep. 2, 1997, now Pat. No. 6,440,455.

(51) Int. Cl.
*A61K 9/127* (2006.01)
*A61K 9/16* (2006.01)
*A61K 31/52* (2006.01)

(52) U.S. Cl. ......................................... 424/450; 514/45

(58) Field of Classification Search ................ 424/450, 424/422, 423, 484, 486, 489–490, 497; 514/45–46
See application file for complete search history.

(56) References Cited

U.S. PATENT DOCUMENTS

| 4,341,868 | A | 7/1982 | Nakanishi et al. |
| 4,883,666 | A | 11/1989 | Sabel et al. |
| 5,187,162 | A | 2/1993 | Marangos et al. |
| 5,250,414 | A | 10/1993 | Schwab et al. |
| 5,422,343 | A | 6/1995 | Yamamoto et al. |
| 5,438,130 | A | 8/1995 | Goldin et al. |
| 5,447,939 | A | 9/1995 | Glasky et al. |
| 6,440,455 | B1 * | 8/2002 | Benowitz ................. 424/450 |

(Continued)

FOREIGN PATENT DOCUMENTS

JP 74015765 4/1974

(Continued)

OTHER PUBLICATIONS

Benowitz, L.I., et al.; *Dept. of Neuroscience Abstracts*; 23(1-2) (1997).

(Continued)

*Primary Examiner*—Gollamudi S. Kishore
(74) *Attorney, Agent, or Firm*—Nixon Peabody LLP

(57) ABSTRACT

Methods for modulating the axonal outgrowth of central nervous system neurons are provided. Methods for stimulating the axonal outgrowth of central nervous system neurons following an injury (e.g., stroke, Traumatic Brain Injury, cerebral aneurism, spinal cord injury and the like) and methods for inhibiting the axonal outgrowth of central nervous system neurons are also provided. Finally, a packed formulation comprising a pharmaceutical composition comprising an inosine nucleoside and a pharmaceutically acceptable carrier packed with instructions for use of the pharmaceutical composition for treatment of a central nervous system disorder is provided.

18 Claims, 9 Drawing Sheets

U.S. PATENT DOCUMENTS 6,551,612 B2 * 4/2003 Benowitz .................... 424/450
6,855,690 B2 * 2/2005 Benowitz ...................... 514/2

FOREIGN PATENT DOCUMENTS

| RU | 2063753 | 7/1996 |
| --- | --- | --- |
| WO | WO 94/00132 | 1/1994 |
| WO | WO 97/03652 | 2/1997 |
| WO | WO 88/09335 | 12/1998 |

OTHER PUBLICATIONS

Bold, J.M., et al.; *Br. J. Pharmac.*; 84:689-696 (1985).
Braumann, T., et al.; *J. of Neurochem.*; 912-919 (1986).
Christjanson, L.J., et al.; *GLIA*; 7:176-182 (1993).
Greene, L.A., et al.; *J. of Neuroscience*; 10(5):1479-1485 (1990).
Gysbers, J.W., et al.; *NeuroReport*; 3(11):997-1000 (1992).
Gysbers, J.W., et al.; *Int. J. Dev. Neuroscience*; 14(1):19-34 (1996).
Hayashi, E., et al.; *Euro. J. of Pharmac.*; 48:297-307 (1978).
Huffaker, T., et al.; *J. of Cellular Physiology*; 120:188-196 (1984).
Juhasz-Nagy, A., et al.; *J. of Pahrac. And Experimental Therapeutics*; 202(3):683-695 (1977).
Matz, H., et al.; *J. of Neuroscience Research*; 24:260-267 (1989).
Nagasawa, H., et al.; *Neuroscience Letters*; 133:129-132 (1991).
Rathbone, M.P., et al.; *Medical Hypotheses*; 37:232-240 (1992).
Rolls, E.T., et al.; *Physiology & Behavior*; 59(4/5):991-1000 (1996).
Satoh, T., et al.; *Mol. Cell Biol.*; 7(12):4553-4556 (1987).
Schwalb, J.M., et al.; *Neuroscience*; 72(4):901-910 (1996).
Schwalb, J.M., et al.; *J. of Neuroscience*; 15(8):5514-5525 (1995).
Standaert, F.G., et al.; *J. of Pharmac. And Experimental Therapeutics*; 199(3):544-552 (1976).
Svensson, B., et al.; *Euro. J. of Neuroscience*; 5:1017-1023 (1993).
Volonte, C., et al.; *The J. of Cell Bio.*; 109:2395-2403 (1989).
Wakade, T.D., et al.; *J. of Physiology*; 488(1):123-138 (1995).
Zarbin, M.A.; et al.; *Exp. Brain Res.*; 81:267-278 (1990).
Zurn, A.D., et al.; *Proc. Natl. Acad. Sci. USA*; 85:8301-8305 (1998).
Takeo et al.; *J. Mol. Cell. Cardiol.*; 20(3):187-199 (1998).

\* cited by examiner

METHODS FOR MODULATING THE AXONAL OUTGROWTH OF CENTRAL NERVOUS SYSTEM NEURONS

CROSS-REFERENCE TO RELATED APPLICATIONS

The present Continuation application claims the benefit under 35 U.S.C. §120 of U.S. Ser. No. 10/385,031 filed on Mar. 10, 2003 now abandoned, which is a Continuation of U.S. Ser. No. 09/997,687 filed on Nov. 29, 2001 now abandoned, which is a Continuation of U.S. Ser. No. 08/921, 902 filed on Sep. 2, 1997, now U.S. Pat. No. 6,440,455.

GOVERNMENT FUNDING

Work described herein was supported, at least in part, under grant R01EY05690 awarded by the National Eye Institute. The U.S. government therefore may have certain rights in this invention.

BACKGROUND OF THE INVENTION

Past early childhood, injury to the central nervous system (CNS) results in functional impairments that are largely irreversible. Within the brain or spinal cord, damage resulting from stroke, trauma, or other causes can result in life-long losses in cognitive, sensory and motor functions, and even maintenance of vital functions. Nerve cells that are lost are not replaced, and those that are spared are generally unable to regrow severed connections, although a limited amount of local synaptic reorganization can occur close lo the site of injury. Functions that are lost are currently untreatable.

Regenerative failure in the CNS has been attributed to a number of factors, which include the presence of inhibitory molecules on the surface of glial cells that suppress axonal growth; absence of appropriate substrate molecules such as laminin to foster growth and an absence of the appropriate trophic factors needed to activate programs of gene expression required for cell survival and differentiation.

By contrast, within the peripheral nervous system (PNS), injured nerve fibers can regrow over long distances, with eventual excellent recovery of function. Within the past 15 years, neuroscientists have come to realize that this is not a consequence of intrinsic differences between the nerve cells of the peripheral and central nervous system; remarkably, neurons of the CNS will extend their axons over great distances if given the opportunity to grow through a grafted segment of PNS (e.g., sciatic nerve). Therefore, neurons of the CNS retain a capacity to grow if given the right signals from the extracellular environment. Factors which contribute to the differing growth potentials of the CNS and PNS include partially characterized, growth-inhibiting molecules on the surface of the oligodendrocytes that surround nerve fibers in the CNS, but which are less abundant in the comparable cell population of the PNS (Schwann cells); molecules of the basal lamina and other surfaces that foster growth in the PNS but which are absent in the CNS (e.g., laminin); and trophic factors, soluble polypeptides which activate programs of gene expression that underlie cell survival and differentiation. Although such trophic factors are regarded as essential for maintaining the viability and differentiation of nerve cells, the particular ones that are responsible for inducing axonal regeneration in the CNS remain uncertain. As a result, to date, effective treatments for CNS injuries have not been developed.

Accordingly, methods and compositions for modulating the outgrowth of CNS neurons are still needed.

SUMMARY OF THE INVENTION

The present invention provides methods and compositions for modulating the axonal outgrowth of central nervous system neurons. The invention is based, at least in part, on the discovery that purine nucleosides and analogs thereof are capable of modulating (i.e. either stimulating or inhibiting) axonal outgrowth of CNS neurons. Accordingly, the method of the invention involves contacting central nervous system neurons with a purine nucleoside or analog thereof. In one aspect, the invention provides methods for stimulating outgrowth, preferably using inosine or guanosine nucleosides or analogs thereof. In another aspect, the invention provides methods for inhibiting outgrowth, preferably using a 6-thioguanine nucleoside. In a preferred embodiment, the methods of the invention modulate axonal outgrowth of retinal ganglion cells.

The invention also provides methods for stimulating the outgrowth of central nervous system neurons following damage or other injury to the CNS neurons (e.g., stroke, Traumatic Brain Injury, cerebral aneurism, spinal cord injury and the like). These methods involve administering to a subject a purine nucleoside (e.g., inosine or guanosine), or analog thereof, such that axonal outgrowth is stimulated. In one aspect, the purine nucleoside or analog thereof is administered by introduction into the central nervous system of the subject, for example into the cerebrospinal fluid of the subject. In certain aspects of the invention, the purine nucleoside or analog thereof is introduced intrathecally, for example into a cerebral ventricle, the lumbar area, or the cisterna magna. In a preferred embodiment, the stimulatory method of the invention promotes outgrowth of damaged retinal ganglion cells. The purine nucleoside or analog thereof can be administered locally to retinal ganglion cells to stimulate axonal outgrowth.

In another embodiment, the invention provides methods for inhibiting outgrowth of CNS neurons in which a purine nucleoside (e.g., 6-thioguanine) is administered to a subject. The inhibitory methods of the invention can be used to inhibit axonal outgrowth in, for example, neuroproliferative disorders or neuropathic pain syndromes.

In yet another aspect of the invention, the purine nucleoside or analog thereof is administered in a pharmaceutically acceptable formulation. The pharmaceutically acceptable formulation can be a dispersion system, for example a lipid-based formulation, a liposome formulation, or a multivesicular liposome formulation. The pharmaceutically acceptable formulation can also comprise a polymeric matrix, selected, for example, from synthetic polymers such as polyesters (PLA, PLGA), polyethylene glycol, poloxomers, polyanhydrides, and pluronics or selected from naturally derived polymers, such as albumin, alginate, cellulose derivatives, collagen, fibrin, gelatin, and polysaccharides.

In a further aspect of the invention, the pharmaceutically acceptable formulation provides sustained delivery, e.g., "slow release" of the purine nucleoside to a subject for at least one, two, three, or four weeks after the pharmaceutically acceptable formulation is administered to the subject. Sustained delivery of a formulation of the invention may be provided by use of, for example, slow release capsules or an infusion pump.

The invention, finally, provides a pharmaceutical composition comprising a purine nucleoside or analog thereof and a pharmaceutically acceptable carrier.

Other features and advantages of the invention will be apparent from the following detailed description, and from the claims.

BRIEF DESCRIPTION OF THE DRAWINGS

FIG. 1A is a graph depicting axonal growth in response to the nucleosides adenosine (A), guanosine (G), cytidine (C), uridine (U), and thymidine (T) at a concentration of 1, 10, and 100 μM as indicated. Data are normalized by subtracting the level of growth in the negative controls and then dividing by the net growth in positive controls treated with 20-30% AF-1.

FIG. 1B is a graph depicting dose-response curves for adenosine and guanosine. $EC_{50}$ values estimated from these data are 10-15 μM for adenosine and 20-30 μM for guanosine.

FIG. 1C is a graph depicting the effects of adenosine nucleotides.

FIG. 1D is a graph depicting the effects of membrane-permeable analogs of cyclic AMP (dBCAMP, dibutyryl cyclic AMP; Sp-8-Br-cAMPS, 8-bromoadenosine-3',5' cyclic monophosphorothioate) or cyclic GMP (8-Br cGMP, 8-bromo cyclic GMP; 8-pcpt-cGMP, 8-(4-chlorophenylthio) guanosine-3',5'-cyclic monophosphate). Data represent means+standard errors of the mean (SEM; not shown if <0.02) and are pooled from 2-4 independent experiments. p values are based upon 2-tailed t-tests, comparing growth to that of the negative controls. *$p<0.05$; $p<0.01$; *$p<0.001$.

FIG. 7A shows that at 10 μM, the purine analog 6-TG suppressed growth induced by AF-1 below baseline (lane 2 vs. 1: $p<0.001$) and reduced the growth induced by 25 μM inosine (Ino-25) by about 50% (lane 4 vs. 3); Growth induced by higher concentrations of inosine or guaniosine (Guo-100: lanes 8 vs. 7) were unaffected. Inosine at 100 μM restored all of the growth induced by AF-1 in the presence of 10 μM 6-TG (lane 10), which is significantly higher than the growth induced by 100 μM inosine, either alone or with 10 μM 6-TG ($p<0.01$).

FIG. 7B is a graph showing that the concentration of 6-TG used here had no effect on cell survival.

FIG. 7C is a graph showing that AF-1 and inosine have partially additive effects. Outgrowth was assessed for AF-1 and inosine, each at 0, $EC_{50}$, or saturating concentrations. While the effects of half-maximal concentrations of each were additive (lane 5), growth reached a plateau level in the presence of higher concentrations of each (lanes 6, 8, 9).

FIG. 7D shows further studies on the effects of 6-thioguanine. Outgrowth stimulated by AF-1 was completely blocked by 6-TG (10 μM) and was not restored in the presence of NBTI (N, 20 μM) and/or dipyridamole (D, 10 μM), purine transport blockers inhibitors that suppress the activity of inosine. Inhibitory effects of 6-TG were not mimicked by two reducing agents, a-tocopherol (α-toc, 30 μM) or glutathione a-methyl ester (MEG, 100 μM).

DETAILED DESCRIPTION

Figure 1A:
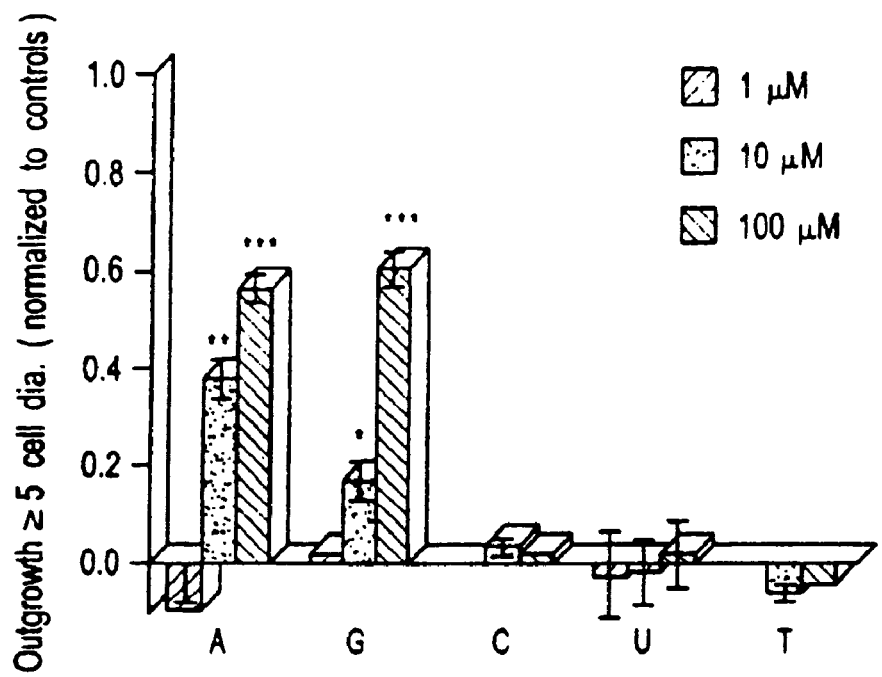
FIGS. 1A-D are graphs showing the quantitation of purinergic effects on axonal outgrowth.

The present invention provides methods for modulating the axonal outgrowth of central nervous system neurons. The invention is based, at least in part, on the discovery that purine nucleosides (e.g., inosine and guanosine) and analogs thereof induce stimulation of axonal outgrowth from both goldfish as well as mammalian retinal ganglion cells (see Examples I and XI, respectively). As shown in Example II, purine nucleosides are more active than their nucleotide counterparts, and they exert their effect through an intracellular pathway (see Example VI). The invention further is based, at least in part, on the discovery that adenosine nucleosides and analogs thereof induce inhibition of axonal outgrowth from retinal ganglion cells (see Example X).

Accordingly, the methods of the invention for modulating axonal outgrowth of CNS neurons generally involve contacting the central nervous system neurons with a purine nucleoside or analog thereof such that axonal outgrowth is modulated.

As used herein, the language "modulating the axonal outgrowth of central nervous system neurons" is intended to include the capacity to stimulate or inhibit axonal outgrowth of central nervous system neurons to various levels, e.g., to levels which allow for the treatment of targeted CNS injuries.

As used herein, the term "outgrowth" refers to the process by which axons grow out of a CNS neuron. The outgrowth can result in a totally new axon or the repair of a partially damaged axon. Outgrowth is typically evidenced by extension of an axonal process of at least 5 cell diameters in length.

As used herein, the term "CNS neurons" is intended to include the neurons of the brain and the spinal cord which are unresponsive to nerve growth factor (NGF). The term is not intended to include support or protection cells such as astrocytes, oligodentrocytes, microglia, ependyma and the like, nor is it intended to include peripheral nervous system (e.g., somatic, autonomic, sympathetic or parasympathetic nervous system) neurons. Preferred CNS neurons are mammalian neurons, more preferably human neurons.

As used herein, the language "contacting" is intended to include both in vivo or in vitro methods of bringing a purine nucleoside or analog thereof into proximity with a CNS neuron, such that the purine nucleoside or analog thereof can modulate the outgrowth of axonal processes from said CNS neuron.

As used herein, the language "purine nucleoside" is art recognized and is intended to include any purine base linked to a sugar, or an analog thereof. For example, purine nucleosides include guanine, inosine or adenine and analogs include 6-thioguanine (6-TG) and the like.

In one embodiment, the outgrowth of CNS neurons is stimulated, preferably using inosine or guanosine nucleosides or analogs thereof. In another embodiment, the outgrowth of CNS neurons is inhibited, preferably using a 6-TG nucleoside.

The invention also provides methods for stimulating the outgrowth of central nervous system neurons following an injury. The method involves administering to a subject a purine nucleoside (e.g., inosine or guanosine) or analog thereof.

As used herein, the term "subject" is intended to include animals susceptible to CNS injuries, preferably mammals, most preferably humans. In a preferred embodiment, the subject is a primate. In an even more preferred embodiment, the primate is a human. Other examples of subjects include dogs, cats, goats, and cows.

As used herein, the term "injury" is intended to include a damage which directly or indirectly affects the normal functioning of the CNS. For example, the injury can be damage to retinal ganglion cells; a traumatic brain injury; a stroke related injury; a cerebral aneurism related injury; a spinal cord injury, including monoplegia, diplegia, paraplegia, hemiplegia and quadriplegia; a neuroproliferative disorder or neuropathic pain syndrome.

As used herein, the term "stroke" is art recognized and is intended to include sudden diminution or loss of consciousness, sensation, and voluntary motion caused by rapture or obstruction (e.g. by a blood clot) of an artery of the brain.

As used herein, the term "Traumatic Brain Injury" is art recognized and is intended lo include the condition in which, a traumatic blow to the head causes damage to the brain, often without penetrating the skull. Usually, the initial trauma can result in expanding hematoma, subarachnoid hemorrhage, cerebral edema, raised intracranial pressure (ICP), and cerebral hypoxia, which can, in turn, lead to severe secondary events due lo low cerebral blood flow (CBF).

Pharmaceutically Acceptable Formulations

In the method of the invention, the purine nucleoside or analog thereof can be administered in a pharmaceutically acceptable formulation. The present invention pertains to any pharmaceutically acceptable formulations, such as synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable formulations comprise a polymeric matrix.

The terms "polymer" or "polymeric" are art-recognized and include a structural framework comprised of repeating monomer units which is capable of delivering a purine nucleoside or analog thereof such that treatment of a targeted condition, e.g., a CNS injury, occurs. The terms also include co-polymers and homopolymers e.g., synthetic or naturally occurring. Linear polymers, branched polymers, and cross-linked polymers are also meant to be included.

For example, polymeric materials suitable for forming the pharmaceutically acceptable formulation employed in the present invention, include naturally derived polymers such as albumin, alginate, cellulose derivatives, collagen, fibrin, gelatin, and polysacchanides, as well as synthetic polymers such as polyesters (PLA, PLGA), polyethylene glycol, poloxomers, polyanhydrides, and pluronics. These polymers are biocompatible with the nervous system, including the central nervous system, they are biodegradable within the central nervous system without producing any toxic byproducts of degradation, and they possess the ability to modify the manner and duration of purine nucleoside release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection.

Polymers can be prepared using methods known in the art (Sandler. S. R.; Karo, W. *Polymer Syntheses*; Harcourt Brace: Boston, 1994; Shalaby, W.; Ikada, Y.; Langer, R.; Williams, J. *Polymers of Biological and Biomedical Significance* (*ACS Symposium Series* 540; American Chemical Society: Washington, D.C. 1994). Polymers can be designed to be flexible; the distance between the bioactive side-chains and the length of a linker between the polymer backbone and the group can be controlled. Other suitable polymers and methods for their preparation are described in U.S. Pat. Nos. 5,455,044 and 5,576,018, the contents of which are incorporated herein by reference.

The polymeric formulations are preferably formed by dispersion of the purine nucleoside within liquefied polymer, as described in U.S. Pat. No. 4,883,666, the teachings of which are incorporated herein by reference or by such methods as bulk polymerization, interfacial polymerization, solution polymerization and ring polymerization as described in Odian G., Principles of Polymerization and ring opening polymerization, 2nd ed., John Wiley & Sons, New York, 1981, the contents of which are incorporated herein by reference. The properties and characteristics of the formulations are controlled by varying such parameters as the reaction temperature, concentrations of polymer and purine nucleoside, types of solvent used, and reaction times.

In addition to the purine nucleoside and the pharmaceutically acceptable polymer, the pharmaceutically acceptable formulation used in the method of the invention can comprise additional pharmaceutically acceptable carriers and/or excipients. As used herein, "pharmaceutically acceptable carrier" includes any and all solvents, dispersion media, coatings, antibacterial and anti fungal agents, isotonic and absorption delaying agents, and the like that are physiologically compatible. For example, the carrier can be suitable for injection into the cerebrospinal fluid. Excipients include pharmaceutically acceptable stabilizers and disintegrants.

The purine nucleoside or analog thereof can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 millimeters or less in diameter, usually 500 microns or less in diameter. Particles less than 1 micron are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 µm, preferably less than 20 µm, and more preferably between about 0.1 and 10 µm.

In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or "MLV"). unilamellar liposomes, including small unilamellar liposomes (also known as unilamellar vesicles or "SUV") and large unilamellar liposomes (also known as large unilamellar vesicles or "LUV"), can all be used so long as a sustained releaserate of the encapsulated purine nucleoside or analogue thereof can be established. In one embodiment, the lipid-based formulation can be a multivesicular liposome system. Methods of making controlled release multivesicular liposome drug delivery systems is described in PCT Application Serial Nos. US96/11642, US94/12957 and US94/04490, the contents of which are incorporated herein by reference.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used.

In preparing lipid-based vesicles containing a purine nucleoside or analogue thereof, such variables as the efficiency of purine nucleoside encapsulation, lability of the purine nucleoside, homogeneity and size of the resulting population of vesicles, purine nucleoside-to-lipid ratio, permeability, instability of the preparation, and pharmaceutical acceptability of the formulation should be considered (see Szoka, et al., *Annual Reviews of Biophysics and Bioengineering,* 9:467, 1980; Deamer, et al., in *Liposomes,* Marcel Dekker, New York, 1983, 27; and Hope, et al., *Chem. Phys. Lipids,* 40:89, 1986, the contents of which are incorporated herein by reference).

Administration of the Pharmaceutically Acceptable Formulation

In one embodiment, the purine nucleoside or analog thereof is administered by introduction into the central nervous system of the subject, e.g., into the cerebrospinal fluid of the subject. In certain aspects of the invention, the purine nucleoside or analog thereof is introduced intrathecally, e.g., into a cerebral ventricle, the lumbar area, or the cisterna magna. In another aspect, the purine nucleoside or analog thereof is introduced intraocullarly, to thereby contact retinal ganglion cells.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization, described in U.S. Pat. No. 436,742 the contents of which are incorporated herein by reference.

In one embodiment, the purine nucleoside formulation described herein is administered to the subject in the period from the time of injury to 100 hours, for example within 24, 12 or 6 hours after the injury has occurred.

In another embodiment of the invention, the purine nucleoside formulation is administered into a subject intrathecally. As used herein, the term "intrathecal administration" is intended to include delivering a purine nucleoside formulation directly into the cerebrospinal fluid of a subject, by techniques including lateral cerebroventricular injection through a burrhole or cisternal or lumbar puncture or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of a purine nucleoside to any of the above mentioned sites can be achieved by direct injection of the purine nucleoside formulation or by the use of infusion pumps. For injection, the purine nucleoside formulation of the invention can be formulated in liquid solutions, preferably in physiologically compatible buffers such as Hank's solution or Ringer's solution. In addition, the purine nucleoside formulation may be formulated in solid form and re-dissolved or suspended immediately prior to use. Lyophilized forms are also included. The injection can be, for example, in the form of a bolus injection or continuous infusion (e.g., using infusion pumps) of the purine nucleoside formulation.

In one embodiment of the invention, said purine nucleoside formulation is administered by lateral cerebro ventricular injection into the brain of a subject in the inclusive period from the time of the injury to 100 hours thereafter. The injection can be made, for example, through a burr hole made in the subject's skull. In another embodiment, said encapsulated therapeutic agent is administered through a surgically inserted shunt into the cerebral ventricle of a subject in the inclusive period from the time of the injury to 100 hours thereafter. For example, the injection can be made into the lateral ventricles, which are larger, even though injection into the third and fourth smaller ventricles can also be made.

In yet another embodiment, said purine nucleoside formulation is administered by injection into the cisterna magna, or lumbar area of a subject in the inclusive period from the time of the injury to 100 hours thereafter.

Duration and Levels of Administration

In another embodiment of the method of the invention, the pharmaceutically acceptable formulation provides sustained delivery, e.g., "slow release" of the purine nucleoside to a subject for at least one, two, three, or four weeks after the pharmaceutically acceptable formulation is administered to the subject.

As used herein, the term "sustained delivery" is intended to include continual delivery of a purine nucleoside or analogue thereof in vivo over a period of time following administration, preferably at least several days, a week or several weeks. Sustained delivery of the purine nucleoside or analogue thereof can be demonstrated by, for example, the continued therapeutic effect of the purine nucleoside or analogue thereof over time (e.g., sustained delivery of the purine nucleoside or analogue thereof can be demonstrated by continued outgrowth or by continued inhibition of outgrowth of CNS neurons over time). Alternatively, sustained delivery of the purine nucleoside or analogue thereof may be demonstrated by detecting the presence of the purine nucleoside or analogue thereof in vivo over time.

In one embodiment, the pharmaceutically acceptable formulation provides sustained delivery of the purine nucleoside or analogue thereof to a subject for less than 30 days after the purine nucleoside or analogue thereof is administered to the subject. For example, the pharmaceutically acceptable formulation, e.g., "slow release" formulation, can provide sustained delivery of the purine nucleoside or analogue thereof to a subject for one, two, three or four weeks after the purine nucleoside or analogue thereof is administered to the subject. Alternatively, the pharmaceutically acceptable formulation may provide sustained delivery of the purine nucleoside or analogue thereof to a subject for more than 30 days after the purine nucleoside or analogue thereof is administered lo the subject.

The pharmaceutical formulation, used in the method of the invention, contains a therapeutically effective amount of the purine nucleoside or analogue thereof. A "therapeutically effective amount" refers to an amount effective, at dosages and for periods of time necessary, to achieve the desired result. A therapeutically effective amount of the purine nucleoside or analogue thereof may vary according to factors such as the disease state, age, and weight of the subject, and the ability of the purine nucleoside or analogue thereof (alone or in combination with one or more other agents) to elicit a desired response in the subject. Dosage regimens may be adjusted to provide the optimum therapeutic response. A therapeutically effective amount is also one in which any toxic or detrimental effects of the purine nucleoside or analogue thereof are outweighed by the therapeutically beneficial effects. A non-limiting range for a therapeutically effective concentration of inosine is 5 µM to 1 mM. A non-limiting range for a therapeutically effective concentration of guanosine is at least 25 µM to 1 mM. In a particularly preferred embodiment, the therapeutically effective concentration of the inosine nucleoside is 10-25 µM, or 25-50 µM. In a particularly preferred embodiment, the therapeutically effective concentration of the guanosine nucleoside is 25-50 µM, 50-100 µM, or 100-150 µM. Adenosine can be used to inhibit neurite outgrowth at relatively high doses, e.g., higher than 5 mM, (so that its conversion to inosine is inhibited). At such concentrations, however, adenosine may become toxic. Adenosine analogs, e.g., 6-thioguanine are, therefore, preferable for administration in mammalian subjects to inhibit axonal growth. It is to be noted that dosage values may vary with the severity of the condition to be alleviated. It is to be further understood that for any particular subject, specific dosage regimens should be adjusted over time according to the individual need and the professional judgment of the person administering or supervising the administration of the purine nucleoside or analogue thereof and that dosage ranges set forth herein are exemplary only and are not intended to limit the scope or practice of the claimed invention.

The invention, in another embodiment, provides a pharmaceutical composition consisting essentially of a purine nucleoside or analog thereof and a pharmaceutically acceptable carrier and methods of use thereof to modulate axonal outgrowth by contacting CNS neurons with the composition. By the term "consisting essentially of" is meant that the pharmaceutical composition does not contain any other modulators of neuronal growth such as, for example, nerve growth factor (NGF). In one embodiment, the pharmaceutical composition of the invention can be provided as a packaged formulation. The packaged formulation may include a pharmaceutical composition of the invention in a container and printed instructions for administration of the composition for treating a subject having a disorder associated with an injury of central nervous system neurons, e.g., an injury to retinal ganglion cells, a spinal cord injury or a traumatic brain injury.

In Vitro Treatment of CNS Neurons

CNS neurons can further be contacted with a therapeutically effective amount of a purine nucleoside or analog thereof, in vitro. Accordingly, CNS neuron cells can be isolated from a subject and grown in vitro, using techniques well known in the art. Briefly, a CNS neuron cell culture can be obtained by allowing neuron cells to migrate out of fragments of neural tissue adhering to a suitable substrate (e.g., a culture dish) or by disaggregating the tissue, e.g., mechanically or enzymatically, to produce a suspension of CNS neuron cells. For example, the enzymes trypsin, collagenase, elastase, hyaluronidase, DNase, pronase, dispase, or various combinations thereof can be used. Trypsin and pronase give the most complete disaggregation but may damage the cells. Collagenase and dispase give a less complete dissaggregation but are less harmful. Methods for isolating tissue (e.g., neural tissue) and the disaggregation of tissue to obtain cells (e.g., CNS neuron cells) are described in Freshney R. I., Culture of Animal Cells, A Manual of Basic Technique, Third Edition, 1994, the contents of which are incorporated herein by reference.

Such cells can be subsequently contacted with a purine nucleoside or analog thereof at levels and for a duration of time as described above. Once modulation of axonal outgrowth has been achieved in the CNS neuron cells, these cells can be re-administered to the subject, e.g., by implantation.

The invention is further illustrated by the following examples, which should not be construed as further limiting. The contents of all references, patents and published patent applications cited throughout this application are hereby incorporated by reference.

EXAMPLES

In the following examples, the following methodologies were used:

Sample Preparation

Axogenesis factor-1 was obtained essentially as described in Schwalb et al., 1995, and Schwalb et al., Neuroscience, 72: 901-910, 1996, the contents of which are incorporated herein by reference). Optic nerves were dissected, cut into fragments 1 mm in length, and incubated in a ratio of 6 nerves in 3 ml of either L-15 media (Gibco BRL) or phosphate-buffered saline (Gibco BRL). After 3-4 hours, nerve fragments were removed by filtering through a 0.22 μm pore low protein-binding filter (Gelman). A low molecular weight fraction of the conditioned media was prepared by ultrafiltration, first with a molecular weight cut-off of 3 kDa (Amicon Centriprep-3), then with a cut-off of 1 kDa (Filtron). The filtrate was used as a positive control at 20-30% final concentration. Adenosine, adenosine 5' monophosphate, adenosine deaminase, adenosine diphosphate, adenosine triphosphate, 8-bromo 3',5'-cyclic guanosine monophosphate, 3',5' cyclic adenosine monophosphate, 5' cyclic guanosine monophosphate, cytidine, guanosine, hypoxanthine, inosine, 5'-inosine monophosphate, a-tocopherol, 6-thioguanine, thymidine, uridine, and xanthine were all obtained from Sigma Chemical Co., St. Louis, Mo., 8-p-sulphophenyl-theophylline, dibutyryl cyclic adenosine monophosphate and 2-deoxycoformycin were from Calbiochem, 2-chloroadenosine, erythro-9-(2-hydroxy-3-nonyl) adenine and IB-MECA from Research Biochemicals, Inc. (Natick, Mass.), and 4-(nitrobenzyl-6-thioinosine) from Aldrich Chemicals, Inc. The membrane-permeable, nonhydrolyzable analogs of cAMP and cGMP 8bromoadenosine-3',5' cyclic monophosphorothioate and 8-(4-chlorophenylthio) guanosine-3',5'-cyclic monophosphate were from Biolog.

Dissociated Retinal Cultures

Goldfish (Comet Variety, Mt. Parnell Fisheries, Mt. Parnell Pa.), 6-10 cm in length, were dark-adapted and their retinas dissected. Retinas were incubated with papain (20 μg/ml), activated with cysteine (2.8 mM) for 30 minutes at room temperature, then dissociated by gentle trituration. Repeated cycles of trituration and sedimentation yielded cultures nearly homogeneous in ganglion cells, which are readily identified by their oval shape, phase-bright appearance, size (diameter 15 μm), and extension of only 1 or 2 neurites of uniform caliber; these criteria have been verified by retrograde labeling (see Schwartz & Agranoff, Brain Res. 206: 331-343, 1981 and Schwalb et al., J. Neuroscience 15: 5514-5625, 1995, the contents of which are incorporated herein by reference). Low density cultures were achieved by plating c. $5 \times 10^3$ cells/well into poly L-lysine coated, 24-well culture dishes (Costar, Cambridge, Mass.). Cells were maintained at 21° C. in serum free, defined media containing insulin, selenium, transferrin, bovine serum albumin, catalase, superoxide dismutase, hormones, and vitamins in Eagle's L-15 media as described in Schwalb et al., 1995, the contents of which are incorporated herein by reference). Dissociated cultures of purified rat retinal ganglion cells were prepared by immunopanning as described in Barres et al., Neuron, 1: 791-803, 1988, the contents of which are incorporated herein by reference). In brief, retinas from postnatal day 8 Sparague-Dawley rats were dissociated using papain activated with cysteine. Macrophages were removed by incubation with an anti-rat macrophage antibody (Accurate) followed by immunopanning with an anti-rabbit 1 gG antibody. Ganglion cells were isolated by immunopanning with an anti-Thy-1 antibody, then dislodged with trypsin for use in low-density cultures. Rat retinal ganglion cells were maintained at 37° C. in a $CO_2$ incubator using the same medium described above except for the presence of 30 mM bicarbonate.

Experimental Design

In a typical experiment, samples were plated in quadruplicate in randomized positions of a 24-well plate and the code was concealed to ensure that growth was evaluated in a blinded fashion. Each experiment contained 4 wells of a negative control (media plus supplements only) and 4 wells of a positive control (a standardized AF-1 sample of known activity). Growth and survival were assessed after 6 days for all ganglion cells in 25 consecutive fields of each well using phase contrast microscopy at 400× magnification (c. 150 ganglion cells counted per well). Extension of a process 5 cell diameters in length was the criterion for growth, since it clearly distinguishes stimulated cells from negative controls (see Schwalb et al., 1995). After the completion of counting, the code was broken, the data tabulated, and means and standard errors were calculated for the 4 replicate wells of each sample using Cricket Graph (CA Associates, Islandia, N.Y.). Data were normalized by subtracting the growth in the negative controls (usually 4-5%) and dividing by the net growth in the positive controls. In the most favorable experiments, more than 50% of retinal ganglion cells (RGCs) exposed to AF-1 extended axons 5 cell diameters in length after 6 days. Group comparisons were based upon pairwise, 2-tailed Student's t-tests. Several independent experiments were performed for most samples, as noted in the figure legends. In some cases, cell viability was assessed with the dye 5,6-carboxyfluorescein diacetate. Cell survival is reported as the number of viable RGCs per high-powered field.

Example I

Figure 1B:
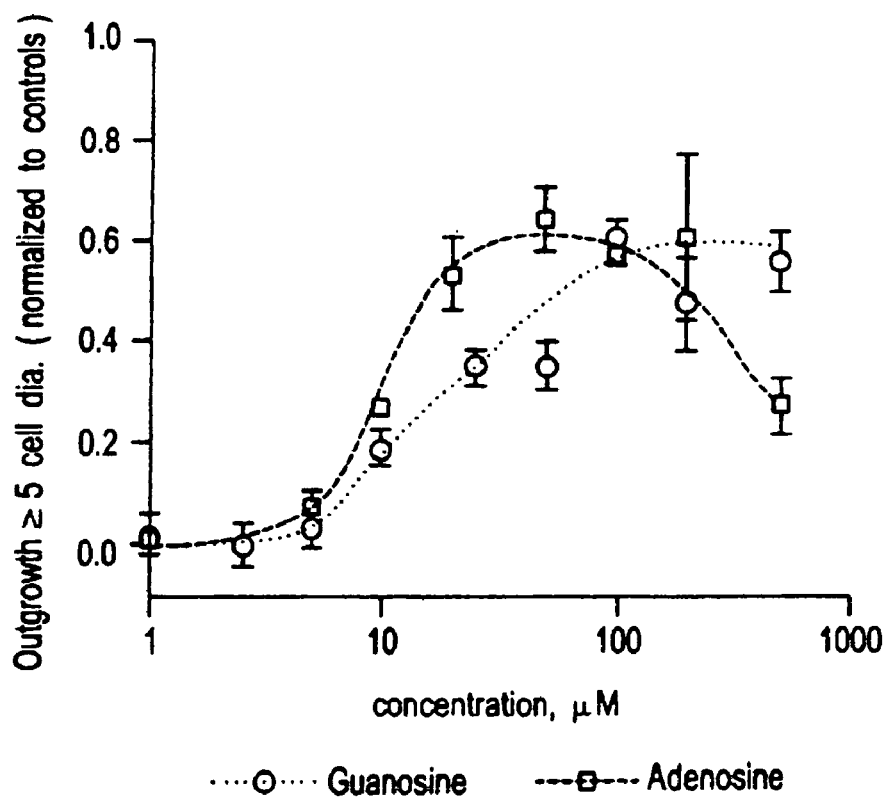
Figure 1C:
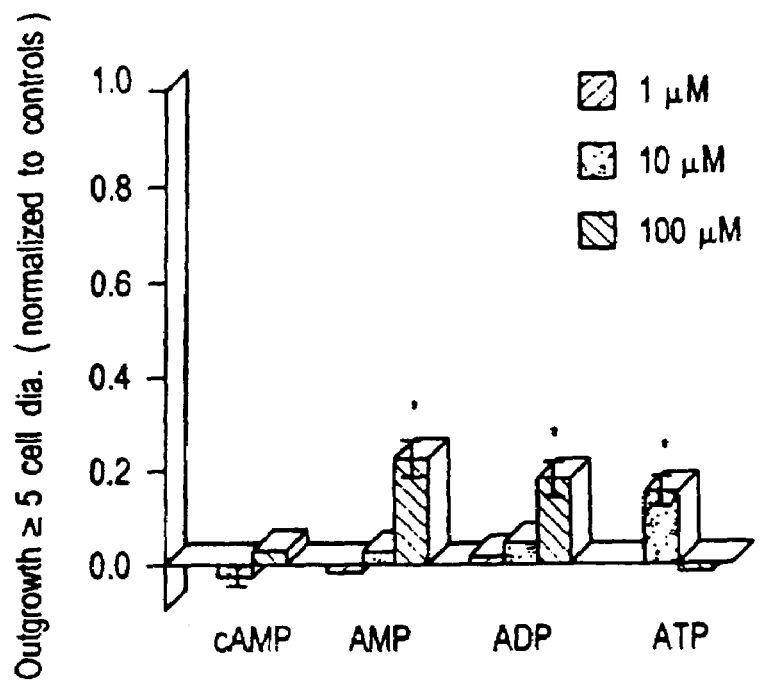

Purine Induced Stimulation of Axonal Outgrowth from Goldfish Retinal Ganglion Cells The low molecular weight growth factor AF-1, secreted by optic nerve glia, induced dramatic outgrowth from goldfish retinal ganglion cells. Little outgrowth occurred in the control condition using defined media alone. These two limits were the basis for normalizing results for other factors. When nucleosides were tested at concentrations between 1-100 μM, adenosine and guanosine stimulated almost as much outgrowth from goldfish retinal ganglion cells as AF-1. Pyrimidine bases had no activity over this concentration range. A more complete dose-response curve for the purines shows that adenosine is the more active of the two, with an $EC_{50}$ of 10-15 μM (see FIG. 1B). At concentrations of 50-100 μM, adenosine induced a maximal response equal to 60% the level induced by AF-1, but at higher concentrations, outgrowth decreased. Guanosine had a higher $EC_{50}$ than adenosine (25 μM, see FIG. 1B), and at concentrations of 100 μM, it stimulated the same maximal level of activity as adenosine, with no obvious decrease in activity at higher concentrations.

Example II

Purine Nucleotides are Less Active than Nucleosides

Figure 1D:
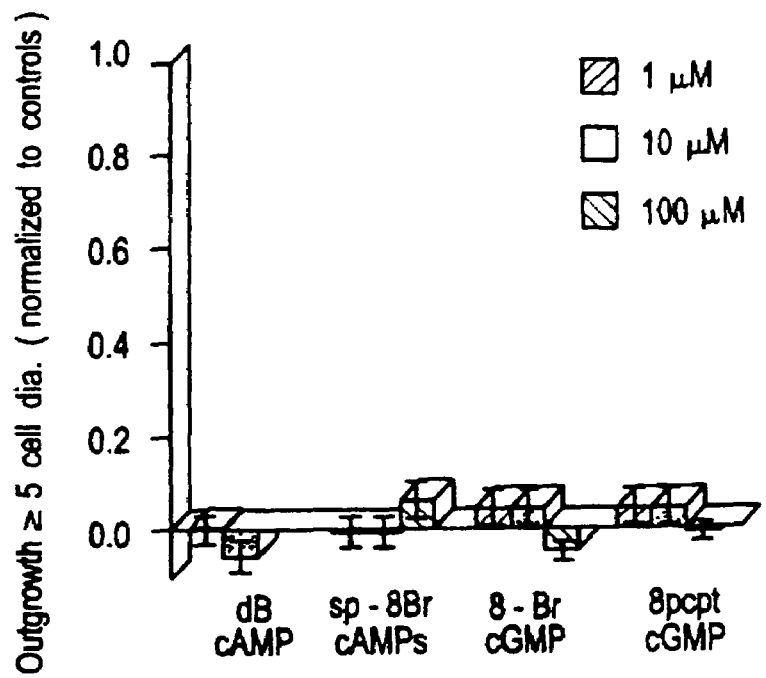

Extracellularly, adenosine could be stimulating either $P_1$ receptors, which are optimally responsive to adenosine per se, or $P_2$ receptors, which respond maximally to ATP or other nucleotides. AMP and ADP showed a marginally significant level of activity at 100 μM (p 0.05), as did ATP at 10 μM (but not at 100 μM). Since the activity of the purine nucleotides is considerably lower than that of the purines themselves, it is unlikely that P2 receptors are involved. Plausibly, the purines could function intracellularly as precursors for cyclic nucleotides that might serve as second messengers in axogenesis. The biological activity of membrane-permeable analogs of cAMP and cGMP was, therefore, examined. Neither dibutyryl cAMP (dBcAMP) nor 8-Br cGMP showed any activity between 1-100 μM (see FIG. 1D). More recently developed nonhydrolyzable, membrane-permeable analogs of cAMP (8-bromoadenosine-3',5' cyclic monophosphorothioate: Sp-8-Br-cAMPS) and cGMP (8-(4-chlorophenylthio) guanosine-3',5'-cyclic monophosphate: 8-pcpt-cGMP)) were also found to be inactive when tested at concentrations up to 1 mM (see FIG. 1D).

Example III

Figure 2:
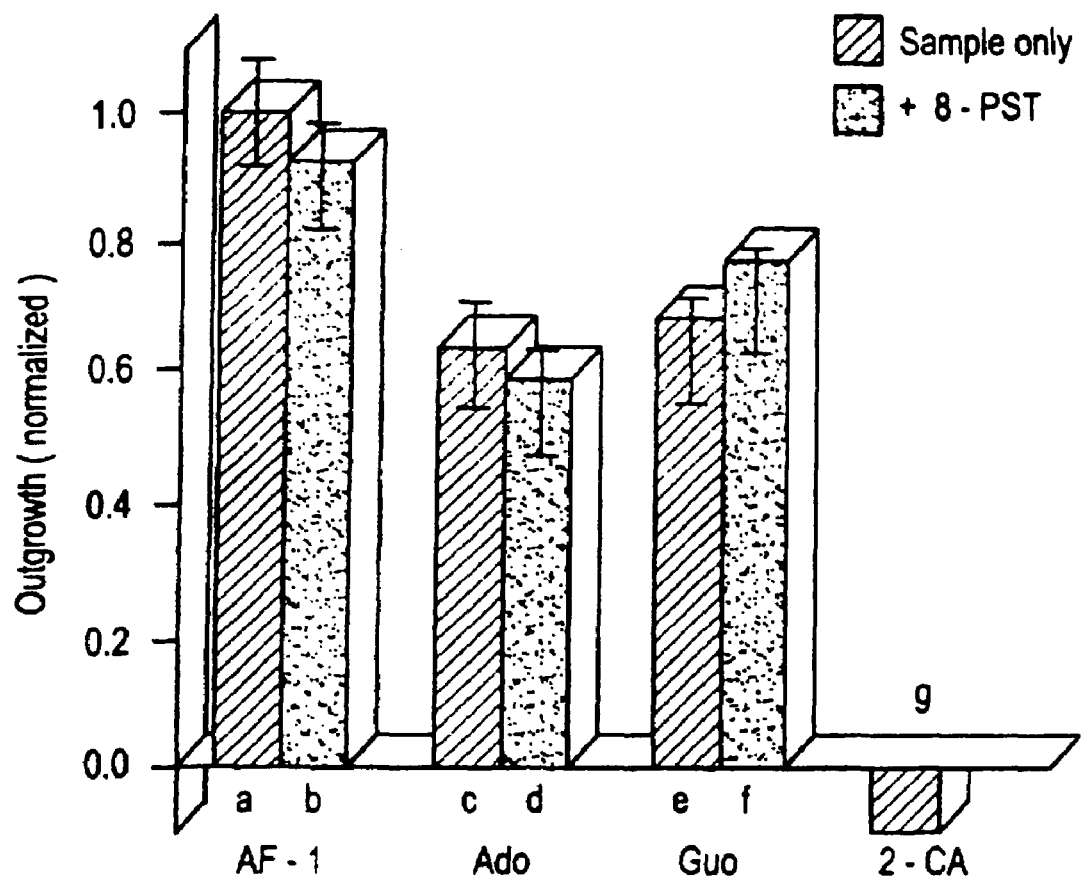
FIG. 2 is a graph showing that adenosine does not stimulate growth via extracellular receptors. Outgrowth stimulated by AF-1 (a-b), 100 μM adenosine (Ado) (c-d), or 100 μM guanosine (Guo) (e-f), is unaffected by the addition of 20 pM 8-PST, an inhibitor of A1 and A2 adenosine receptors (compare growth in a, c, and e with b, d, and f). The nonhydrolyzable adenosine analog, 2-chloroadenosine (2-CA, 100 μM) diminishes growth below baseline levels (g) ($p<0.001$ in 3 experiments).

The Positive Effects of Adenosine are Not Mediated through Extracellular Adenosine Receptors 8-p-(sulfophenyl theophylline) (8-PST), described in Collis et al., Brit. J. Pharmacol. 92:69-75, 1987, the contents of which are incorporated herein by reference, is an inhibitor of the two most common adenosine receptors (A1 and A2). At 20 μM, a dosage that almost completely blocks receptor-mediated effects of adenosine in rats, 8-PST had no effect on outgrowth stimulated by adenosine, guanosine, or AF-1 (see FIG. 2). Further evidence that the positive effects of adenosine are not mediated through extracellular adenosine receptors comes from studies using the non-hydrolyzable analog 2-chloroadenosine (2CA), which is an agonist at the A1, A2 and A3 receptors. At concentrations of 10 and 100 μM, 2-CA caused a small but significant decrease in growth below the baseline in 3 out of 3 independent experiments (see FIG. 2).

Example IV

Adenosine Must be Hydrolyzed to Inosine to Stimulate Growth

Figure 3A:
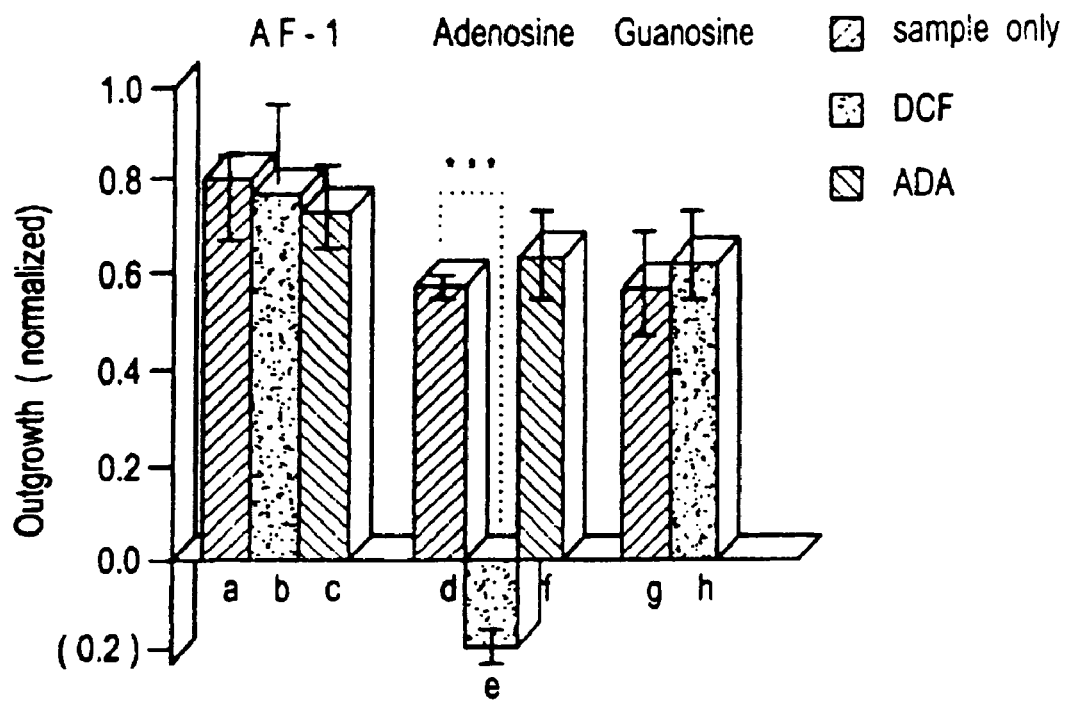
FIG. 3 is a graph showing that adenosine must be hydrolyzed to stimulate outgrowth. Top: A graph depicting the effects of deoxycoformycin (DCF) and exogenous adenosine deaminase (ADA) on outgrowth induced by AF-1 (a-c), adenosine (d-f) and guanosine (g, h); Bottom: A graph depicting the effects of deoxycoformycin (DCF) and exogenous adenosine deaminase (ADA) on survival induced by AF-1 (a-c), adenosine (d-f), and guanosine (g, h). Whereas augmenting adenosine hydrolysis with exogenous ADA leaves the activity of adenosine unaltered (f), blocking endogenous ADA activity with DCF causes adenosine to suppress growth (e, top) and survival (e, bottom). ***$p<0.001$.
Figure 3B:
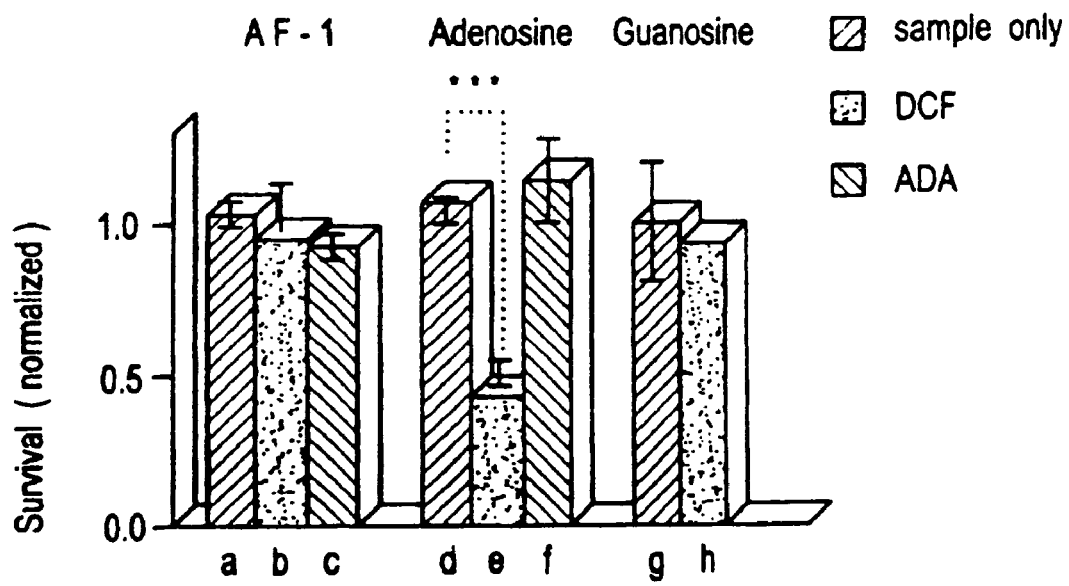

To investigate whether the activity of adenosine is due to the formation of an active metabolite, the activity of ADA was inhibited using either deoxycoformycin (DCF) or erythro-9-(2-hydroxy-3-nonyl)adenine (EHNA). In the presence of 10 μM DCF, 100 μM adenosine not only failed to stimulate growth, but caused it to decline below baseline levels (FIG. 3, lanes e vs. d). Cell survival also decreased when adenosine hydrolysis was blocked. In the presence of 10 μM DCF, 10 μM adenosine caused survival to decrease by 20% (not shown), and 100 μM adenosine caused survival to decline by 57% (FIG. 3, bottom, lane e). The effects of DCF on outgrowth and survival were specifically related to the presence of nonhydrolyzed adenosine, since they did not occur when DCF was used alone, with AF-1, or with guanosine (FIG. 3, lanes b and h). Like DCF, 10 μM EHNA rendered adenosine (100 μM) ineffective in stimulating outgrowth and caused cell survival to decline by about 30% (data not shown). EHNA also exhibited nonspecific effects, however, reducing growth stimulated by either guanosine or AF-1 by about 50%, though not altering cell survival. Further evidence that the positive effects of adenosine require its hydrolysis comes from experiments in which exogenous ADA was added. At 0.4 U/ml, the enzyme did not diminish axon outgrowth stimulated by 100 μM adenosine or affect cell survival (see FIG. 3, lane f).

Example V

Inosine is the Active Metabolite

Figure 4:
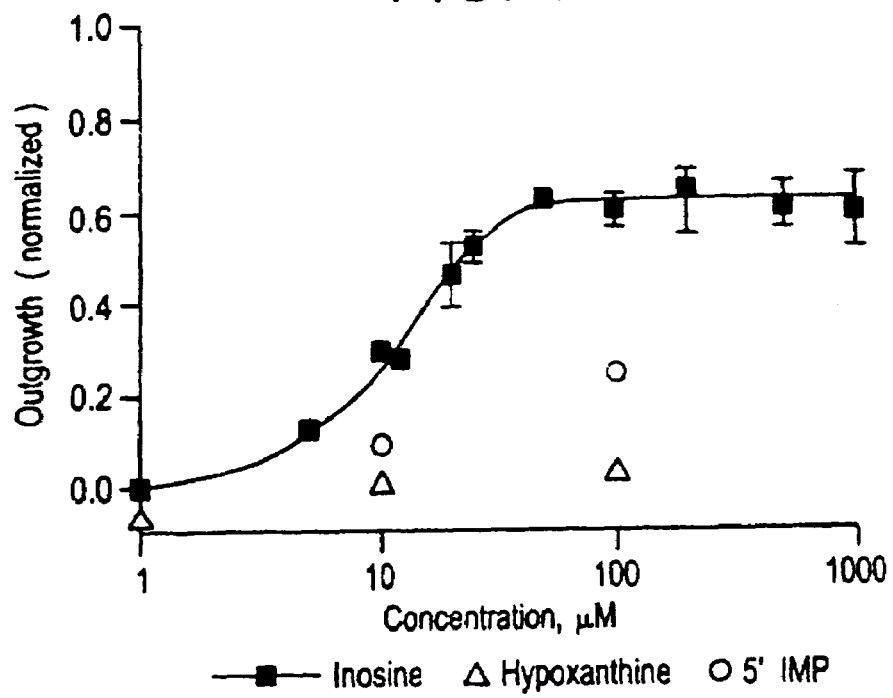
FIG. 4 is a graph depicting a dose-response curve for inosine. At concentrations above 50 μM inosine stimulates about 60% the maximal level of growth achieved with AF-1. The $EC_{50}$ for inosine is estimated to be 10-15 μM. Hypoxanthine was inactive, while 5' IMP appears to have less than 1/10 the activity of inosine. Outgrowth stimulated by all concentrations of inosine 10 μM is significantly above background ($p<0.001$).

Inosine, the primary product of adenosine deamidation, proved to be a potent activator of axon outgrowth. As shown in FIG. 4, the $EC_{50}$ for inosine was 10-15 μM and a maximal response, equal to about 60% the level achieved with AF-1, was attained at concentrations above 25 μM. While the $EC_{50}$ and maximum response induced by inosine were similar to those of adenosine, one notable difference was that at higher concentrations, inosine did not cause growth to decline, unlike the case for adenosine. Further hydrolysis of inosine yields hypoxanthine, which showed no activity at all (see FIG. 4). Inosine 5' monophosphate (5' IMP) was inactive at 10 μM, and at 100 μM it showed less activity than inosine at 10 μM (see FIG. 4).

Example VI

Purines Stimulate Growth through an Intracellular Pathway

Figure 5:
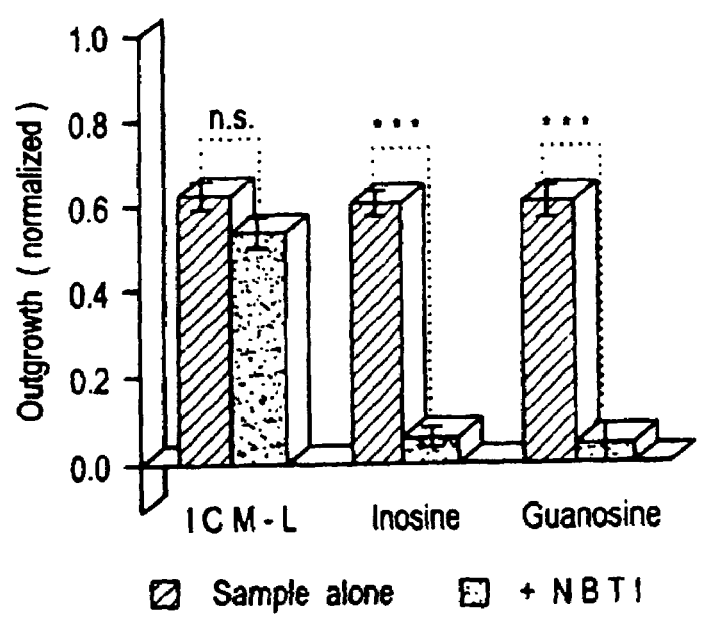
FIG. 5 is a graph depicting that inosine and guanosine stimulate growth through an intracellular mechanism. At 20 μM, NBTI, an inhibitor or purine transport, has no effect on the activity of AF-1, but blocks c. 90% of the activity of inosine (50 μM) or guanosine (100 μM). *** differences in growth with and without drugs are significant at $p<0.001$. Data is pooled from 4 independent experiments.

Two inhibitors of the purine transporter, nitrobenzylthio inosine (NBTI) and dipyridamole, were used to investigate whether inosine and guanosine needed to enter neurons to stimulate outgrowth. At 20 μM, NBTI blocked about 90% of the growth induced by either inosine or guanosine (see FIG. 5; 86% loss of activity for 50 μM inosine, p<0.001; 93% loss of activity for 100 μM guanosine p<0.01). Dipyridamole (10 μM) also diminished the growth induced by inosine (114% decrease; p<0.01; not shown; guanosine not tested). In contrast, AF-1 showed little inhibition by NBTI (10% decline, n.s.) and slightly more with dipyridamole (25% decline, n.s., not shown). The NBTI-related loss in activity for the purines was far greater than for AF-1 (p<0.001).

Example VII

AF-1 Activity is Not Due to Inosine

Figure 6A:
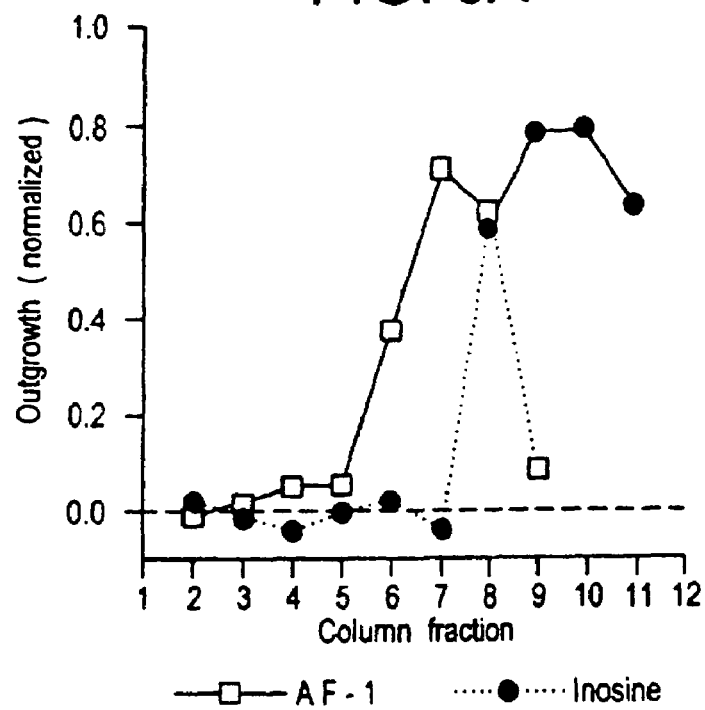
FIG. 6A is a graph showing that AF-1 contains no apparent inosine activity. On a G-10 Sephadex column, AF-1 elutes with a peak of 7 minutes, with no activity detected at the time of peak inosine elution (i.e., 9-10 min).

To address whether AF-1 preparations might still contain purines that could account for some of their biological activity, native AF-1 and inosine were chromatographed on a size-exclusion column with Sephadex G-10 (Pharmacia Biotech, Uppsala, Sweden), 1 cm in diameter and 10 cm in length. Samples were loaded in a volume of 0.5 ml and collected in 1 ml fractions. The column buffet was either 20% methanol in distilled water or 0.14 M NaCl. Fractions were bioassayed at 30% concentration. As shown in FIG. 6A, the peak of inosine activity was at 9-10 minutes, whereas for AF-1 it occurred at 7 minutes.

Example VIII

Figure 6B:
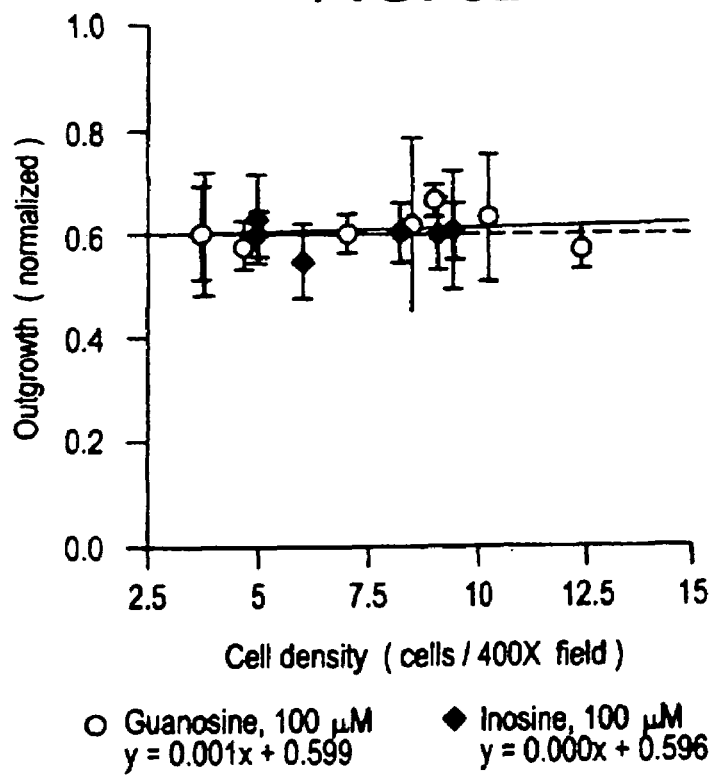
FIG. 6B is a graph showing that the effects of inosine and guanosine are independent of cell density. Data from multiple independent experiments, each indicated by a single point, were analyzed for the effect of plating density on cell outgrowth. In all cases, the concentration of inosine or guanosine was maintained at 100 μM. The regression lines were calculated by least-squares-fit (Cricket Graph) and are shown below the symbols.

Axonal Outgrowth is the Effect of Inosine and Guanosine and Not the Effect of a Secondary Factor The cultures used here contained 70-90% ganglion cells, with the remainder representing other neural and non-neuronal elements of the retina (see Schwartz & Agranoff, 1982 and Schwalb et al, 1995, the contents of which are incorporated herein by reference). This heterogeneity raised the possibility that inosine or guanosine could act first upon another cell population, which secretes a secondary factor that stimulates retinal ganglion cells to grow. In this case, the effect of the purines would be expected to vary with cell density, since the concentration of any secondary factor would increase proportionately with increasing density. To examine this, axonal outgrowth as investigated in response to a fixed concentration of inosine or guanosine over a 3-4 fold range of cell densities. The regression lines for both the inosine and the guanosine data demonstrate that growth is not a function of cell density (see FIG. 6B), arguing against the presence of a concentration-dependent secondary factor.

Example IX

Induction of Phosphoprotein GAP-43 Expression by Purines

One hallmark of optic nerve regeneration in vivo is the enhanced expression of the membrane phosphoprotein GAP-43. To investigate whether this upregulation is induced by purines, immunohistochemistry was carried out using a polyclonal rabbit antiserum against recombinant goldfish GAP-43. Recombinant zebrafish GAP-43 was made by transforming *E. coli* with a cDNA isolated by Dr. Eva Reinhard, University of Basel, Switzerland (see Reinhard et al., Development, 120: 1757-1775, 1994, the contents of which are incorporated herein by reference) subcloned into the prokaryotic expression vector pTrcHisB (Invitrogen). The protein produced was purified by $Ni^{2+}$-NTA-affinity chromatography and used to immunize rabbits. The specificity of the resulting antibody was demonstrated in western blots, where the antibody recognized a unique 48 kDa band that is enriched in retinal ganglion cells undergoing regeneration or in synaptosomal plasma membranes from goldfish brain.

AF-1, inosine, and guanosine all caused a large increase in GAP-43 levels relative to L-15 treated controls. A semi-quantitative analysis was carried out by assigning a level for GAP-43 immunoreactivity of 0 (none), 1 (moderate) or 2 (intense), and correlating the staining intensity with the length of a cell's axon for 150-200 cells treated with L-15, inosine, or AF-1. Inosine produced a 5.5-fold increase in the number of intensely stained cells over L-15, whereas AF-1 produced a 8-fold increase. In all 3 cases, the intensity of GAP-43 immunostaining correlated strongly with axonal length.

Example X

Blockade of Axonal Outgrowth with 6-Thioguanine (6-TG)

Figure 7A:
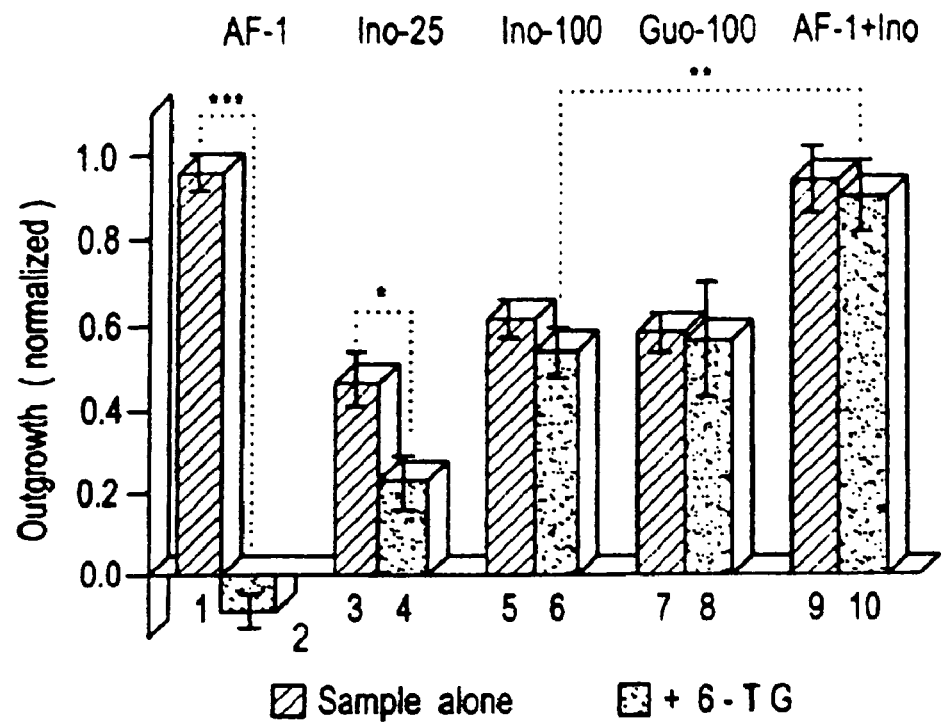
FIGS. 7A-D are graphs showing that the effects of AF-1 are inhibited by 6-thioguanine but restored by inosine.
Figure 7B:
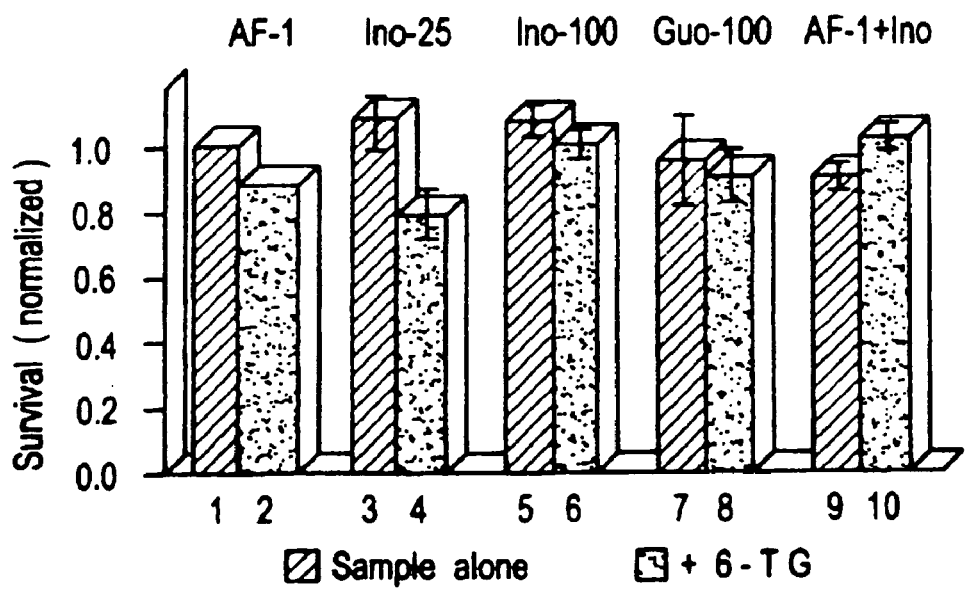
Figure 7C:
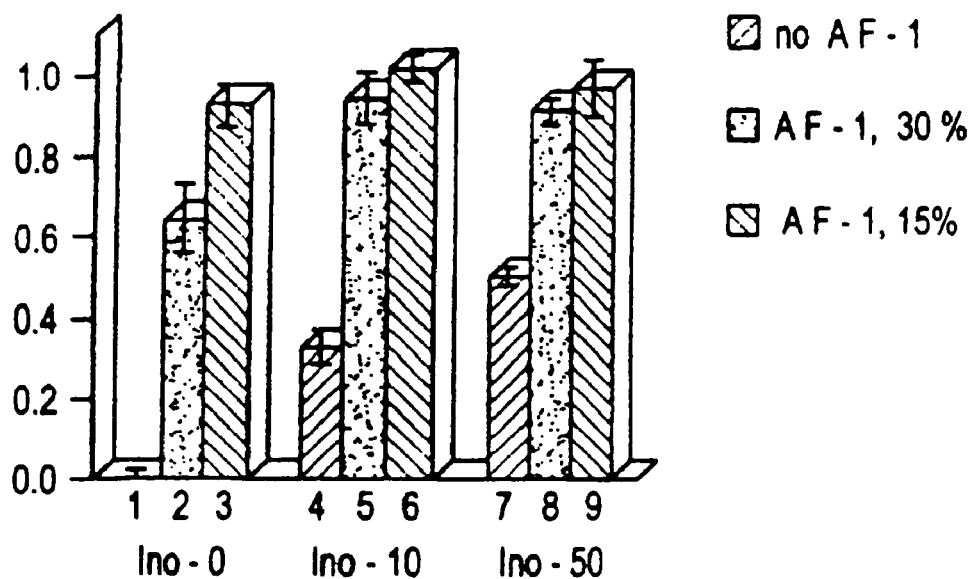
Figure 7D:
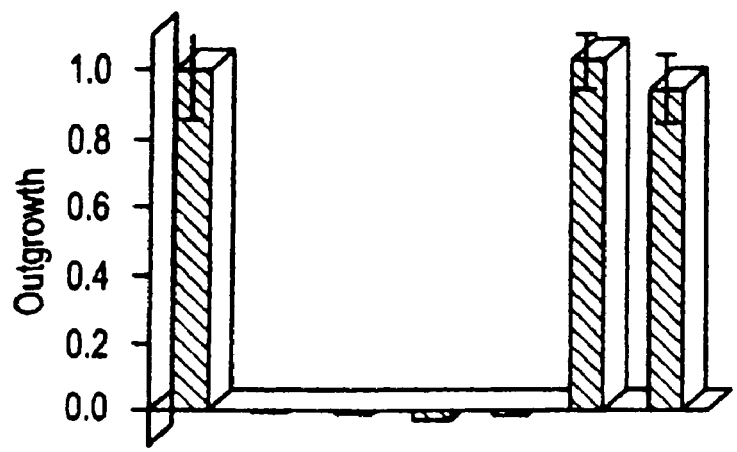

In goldfish RGCs, 6-TG at 10 μM blocked all growth stimulated by AF-1 (see FIG. 7A, lane 2), but had no effect on cell survival (see FIG. 7B). The same concentration of 6-TG reduced outgrowth stimulated by 25 μM inosine by only 50% (see FIG. 7A, lanes 3 and 4), and had no effect on growth stimulated by either 100 μM inosine or 100 μM guanosine (see FIG. 7A. lanes 5-8). At 100 μM inosine fully restored the growth induced by AF-1 in the presence of 10 μM 6-TG back to its original level, which was significantly higher than the level of growth induced by inosine alone (see FIG. 7A, lanes 10 vs. 6). Therefore, inosine and 6-TG appear to be acting competitively at a level of intracellular signaling that is also utilized by AF-1 to stimulate outgrowth. Further evidence that inosine may activate the same pathway that is utilized by AF-1 signaling came from the observation that when the two were combined at their $EC_{50}$ levels, they showed additive effects, whereas at saturating concentrations, growth saturates at the level stimulated by high AF-1 levels alone (see FIG. 7C, lane 9). Since 6-TG has a free thiol, it could be acting as a reducing agent rather than as a purine analog. However, two other reducing agents, a-tocopherol at 30 μM or glutathione a-methyl ester (MEG) at 100 μM had no effect on outgrowth stimulated by AF-1 (see FIG. 7D). Another possibility is that inosine might block the inhibitory effect of 6-TG on outgrowth by interfering with its transport into cells. However, the two transport inhibitors that blocked the activity of inosine, NBTI and dipyridamole, failed to prevent 6-TG from blocking outgrowth stimulated by AF-1 (see FIG. 7D).

Example XI

Mammalian Retinal Ganglion Cells Extend Axons in Response to Inosine

Figure 8:
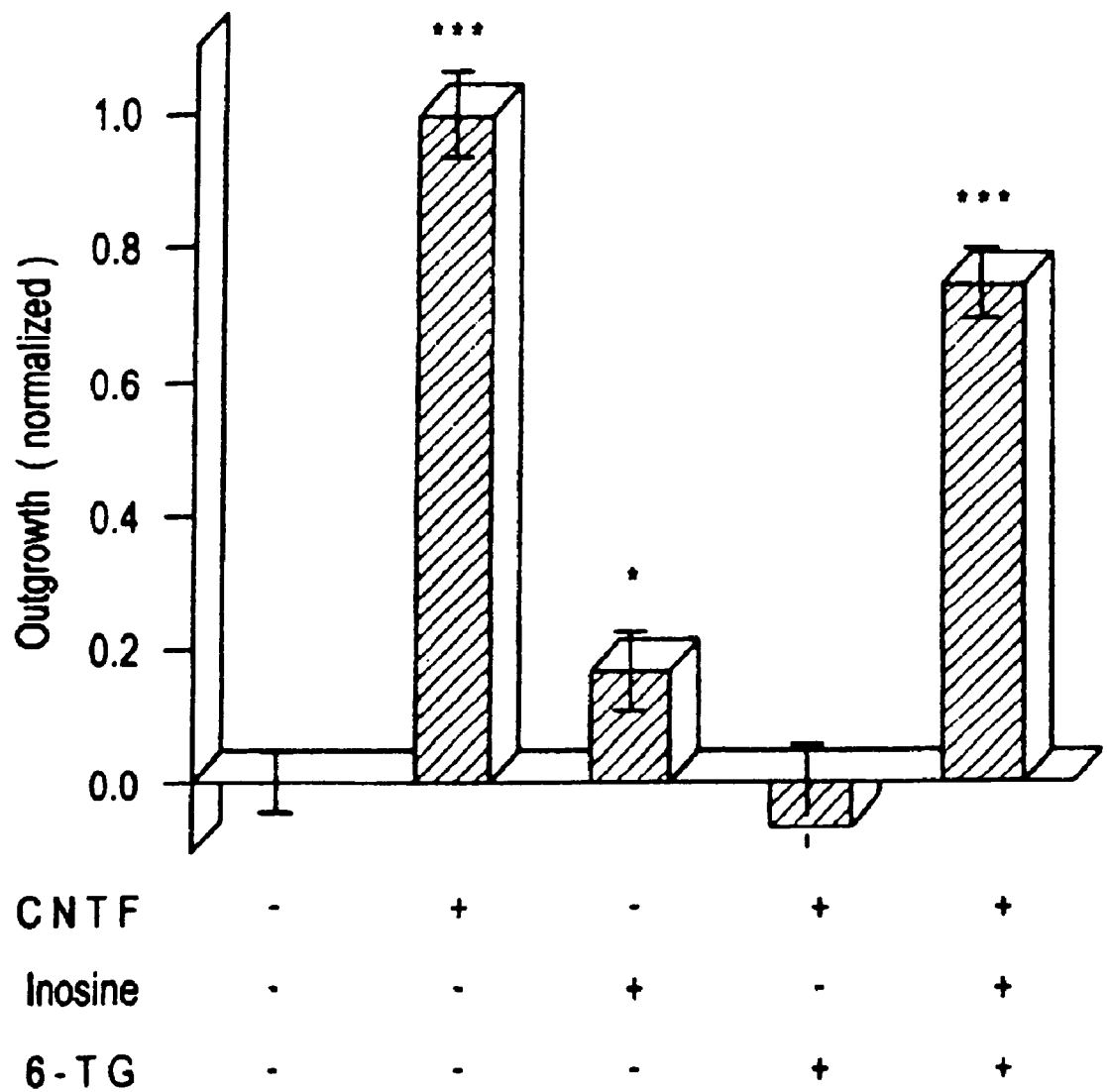
FIG. 8 is a graph depicting the effects of purines on rat retinal ganglion cells (quantitative studies). CNTF stimulated growth is inhibited by 6-TG (10 μM) but is fully restored by the addition of 25 μM inosine. Significance of differences from control: *$p=0.03$; ***$p<0.001$. Results are pooled from 3 independent studies.

Retinal ganglion cells were isolated from 8 day old rats by immunopanning as described in Barres et al., Neuron, 1: 791-803, 1988, the contents of which are incorporated herein by reference, and grown in defined media. Inosine at 25 or 50 μM stimulated a 50% increase in the number of cells extending axons 5 cell diameters in length (see FIG. 8). Ciliary neurotrophic factor (CNTF) induced a much larger increase in outgrowth (see FIG. 8) and enhanced cell survival. At 10 μM, 6-TG blocked CNTF-induced outgrowth. The addition of inosine at 50 μM restored CNTF-induced outgrowth nearly to its original level (see FIG. 8).

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for stimulating the axonal outgrowth of central nervous system neurons following traumatic brain injury in a mammal, comprising intrathecal administration into the central nervous system of the mammal a pharmaceutical composition consisting essentially of an effective amount of inosine such that axonal outgrowth is stimulated in vivo.

2. A method of treating a mammal having suffered a traumatic brain injury which comprises intrathecal administration of a pharmaceutical composition to said mammal, wherein the active ingredient consists of inosine and a pharmaceutically acceptable carrier, and wherein the pharmaceutical composition is administered in a period from the time of the traumatic brain injury to 100 hours after the traumatic brain injury.

3. The method of claim 1, or 2, wherein the inosine is administered to contact CNS neurons in vivo with a concentration of inosine of 5 µM to 1 mM.

4. The method of claim 1, or 2, wherein the pharmaceutical composition is introduced into the cerebral spinal fluid of the mammal.

5. The method of claim 4, wherein the pharmaceutical composition is introduced into a cerebral ventricle.

6. The method of claim 4, wherein the pharmaceutical composition is introduced into the lumbar area.

7. The method of claim 4, wherein the pharmaceutical composition is introduced into the cisterna magna.

8. The method of claim 4, wherein the pharmaceutical composition is administered by the use of an infusion pump.

9. The method of 1, or 2, wherein the pharmaceutical composition is administered continually over a period of at least several days.

10. The method of claim 1, or 2, wherein the pharmaceutical composition is administered continually over a period of at least four weeks.

11. The method of claim 1, or 2, wherein the mammal is human.

12. A method for stimulating the axonal outgrowth of central nervous system neurons following optic nerve injury in a mammal, comprising intrathecal administration into the central nervous system of the mammal a pharmaceutical composition consisting essentially of an effective amount of inosine such that axonal outgrowth is stimulated in vivo.

13. A method of treating a mammal having suffered an optic nerve injury which comprises intrathecal administration of a pharmaceutical composition to said mammal, wherein the active ingredient consists of inosine and a pharmaceutically acceptable carrier, and wherein the pharmaceutical composition is administered in a period from the time of the optic nerve injury to 100 hours after the optic nerve injury.

14. The method of claim 12, or 13, wherein the inosine is administered to contact CNS neurons in vivo with a concentration of inosine of 5 µM to 1 mM.

15. The method of claims 12, or 13, wherein the pharmaceutical composition is administered by the use of an infusion pump.

16. The method of 12, or 13, wherein the pharmaceutical composition is administered continually over a period of at least several days.

17. The method of claim 12, or 13, wherein the pharmaceutical composition is administered continually over a period of at least four weeks.

18. The method of claim 12, or 13, wherein the mammal is human.

* * * * *